(12) United States Patent
Wu et al.

(10) Patent No.: US 10,940,237 B2
(45) Date of Patent: Mar. 9, 2021

(54) TISSUE STRUCTURE SCAFFOLDS

(71) Applicant: University of Durham, Durham (GB)

(72) Inventors: Junjie Wu, Durham (GB); Ross Carnachan, Durham (GB); Stefan Przyborski, Durham (GB)

(73) Assignee: UNIVERSITY OF DURHAM (A GB EDUCATIONAL CORPORATION), Durham (GB)

( * ) Notice: Subject to any disclaimer, the term of this patent is extended or adjusted under 35 U.S.C. 154(b) by 0 days.

(21) Appl. No.: 16/095,420

(22) PCT Filed: May 12, 2017

(86) PCT No.: PCT/EP2017/061542
§ 371 (c)(1),
(2) Date: Oct. 22, 2018

(87) PCT Pub. No.: WO2017/182676
PCT Pub. Date: Oct. 26, 2017

(65) Prior Publication Data
US 2019/0134264 A1 May 9, 2019

(51) Int. Cl.
*A61L 27/26* (2006.01)
*A61L 27/56* (2006.01)
*A61L 27/24* (2006.01)

(52) U.S. Cl.
CPC .............. *A61L 27/26* (2013.01); *A61L 27/24* (2013.01); *A61L 27/56* (2013.01)

(58) Field of Classification Search
None
See application file for complete search history.

(56) References Cited

U.S. PATENT DOCUMENTS 5,652,194 A * 7/1997 Dyer ................... A61F 5/4401
502/402

FOREIGN PATENT DOCUMENTS

WO    WO 2000/34454        6/2000
WO    PCT/EP2017/061542    10/2017

OTHER PUBLICATIONS

Ma et al. "Collagen/chitosan porous scaffolds with improved biostability for skin tissue engineering." Biomaterials 24.26 (2003): 4833-4841. (Year: 2003).*
Barbetta et al. "Enzymatic cross-linking versus radical polymerization in the preparation of gelatin polyHIPEs and their performance as scaffolds in the culture of hepatocytes." Biomacromolecules 7.11 (2006): 3059-3068 (Year: 2006).*
Lee et al. "CO2-in-water emulsion-templated poly (vinyl alcohol) hydrogels using poly (vinyl acetate)-based surfactants." Macromolecules 40.6 (2007): 1955-1961. (Year: 2007).*
Written opinion and search report for PCT/EP2017/061542, dated Oct. 26, 2017, University of Durham.
Carnachan, R., et al. Tailoring the morphology of emulsion-templated porous polymers. Soft Matter 2: 608-616 (2006).
Ko, C-L., et al. Characterization of controlled highly porous hyaluronan/collagen cross-linking sponges for tissue engineering. J Mech Behav Biomed Mater 14: 227-38 (2012).
Ma. L., et al. Collagen/chitosan porous scaffolds with improved biostability for skin tissue engineering. Biomaterials 24: 4833-4841 (2003).
Uygun, B.E., et al. Organ reengineering through development of a transplantable recellularized liver graft using decellularized liver matrix. Nat. Med. 16(7): 814-820 (2010).

* cited by examiner

*Primary Examiner* — Emily A Cordas
(74) *Attorney, Agent, or Firm* — Brian S. Boyer; Syndicated Law, PC.

(57) ABSTRACT

A method of forming a scaffold comprises the steps of: preparing a high internal phase emulsion (HIPE) comprising an aqueous solution of: proteins selected from the group consisting of collagen and mixtures of collagen and chitosan; and a cross-linking agent; by addition of an immiscible solvent to the solution to form the HIPE; reducing the temperature of the HIPE to solidify the HIPE; removing water and solvent by vaporisation at a temperature above the melting point of the solvent to form a porous structure; and before or after removal of solvent, causing cross-linking of the protein with the cross-linking agent to form a crosslinked scaffold structure.

8 Claims, 10 Drawing Sheets

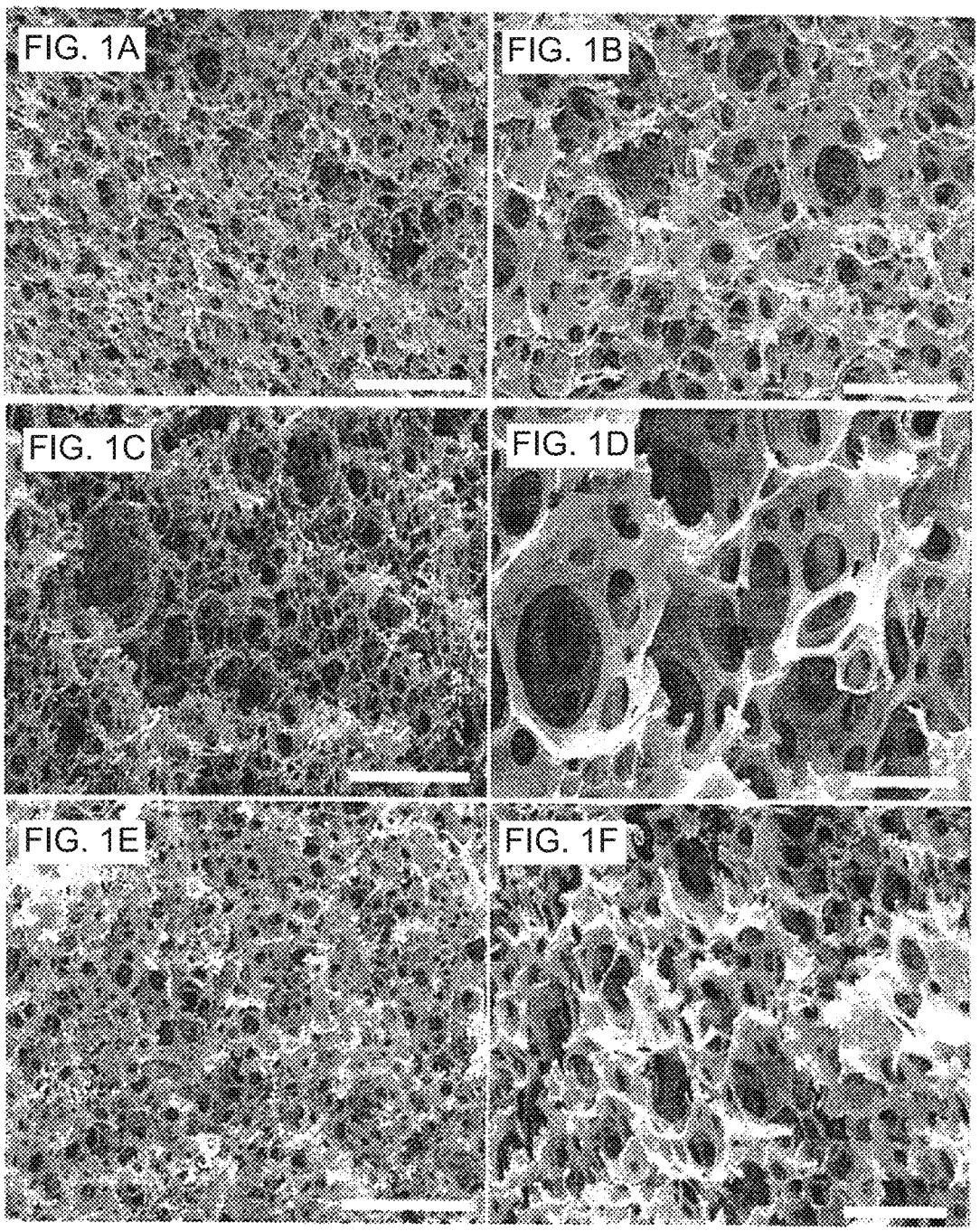

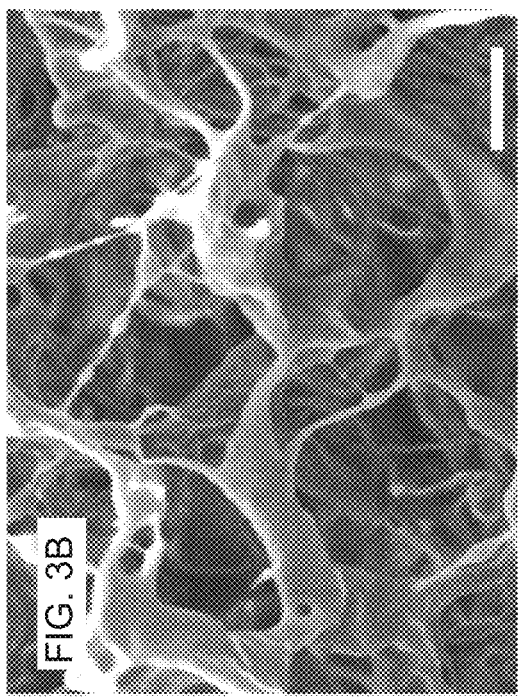
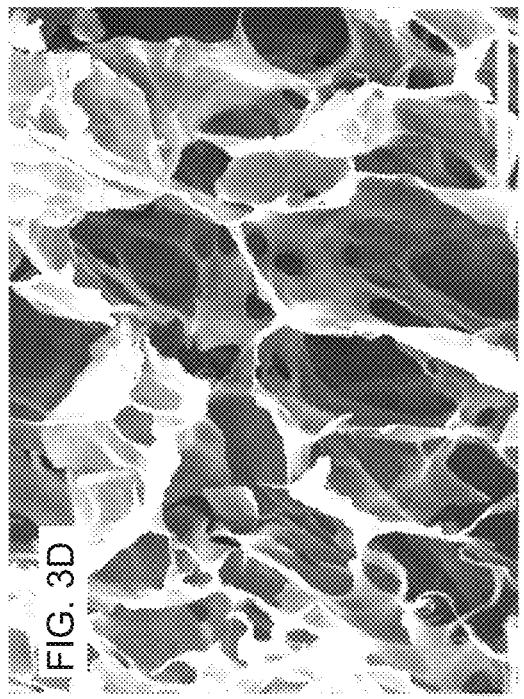
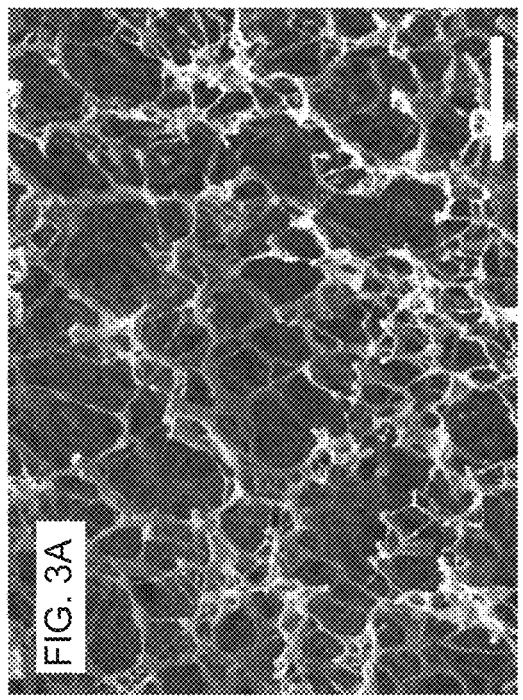
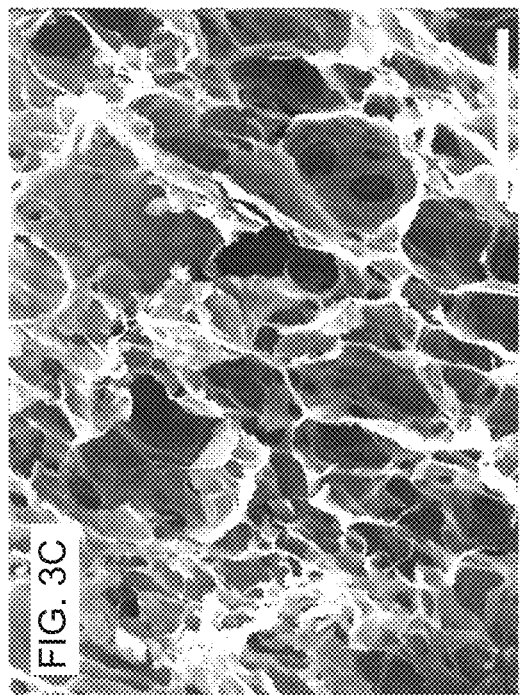
FIG. 3B
FIG. 3D
FIG. 3A
FIG. 3C

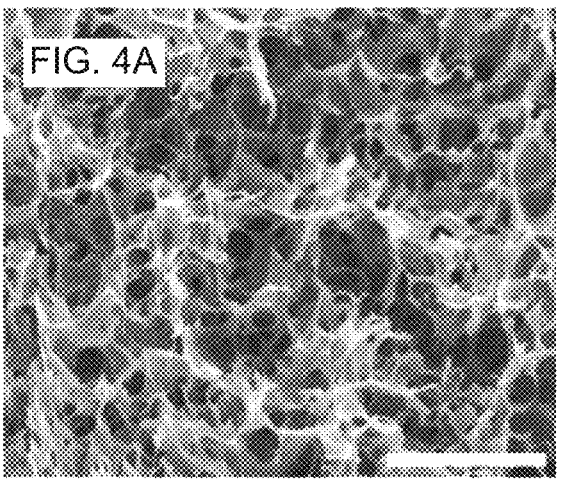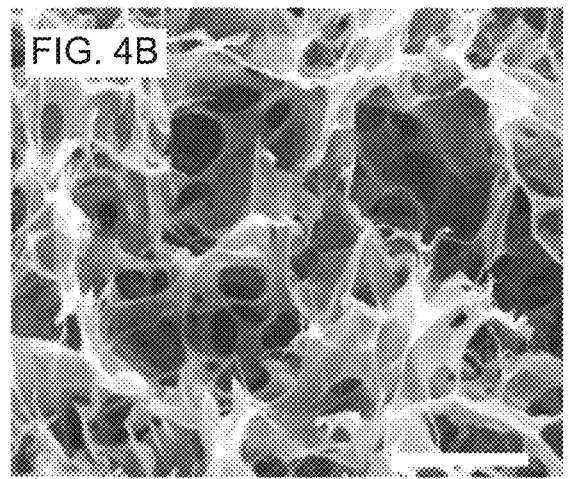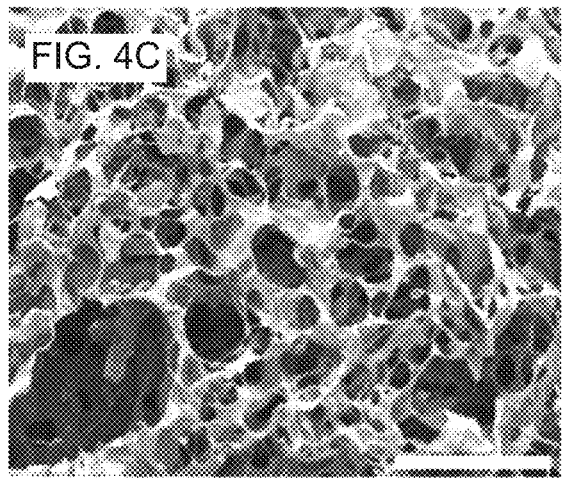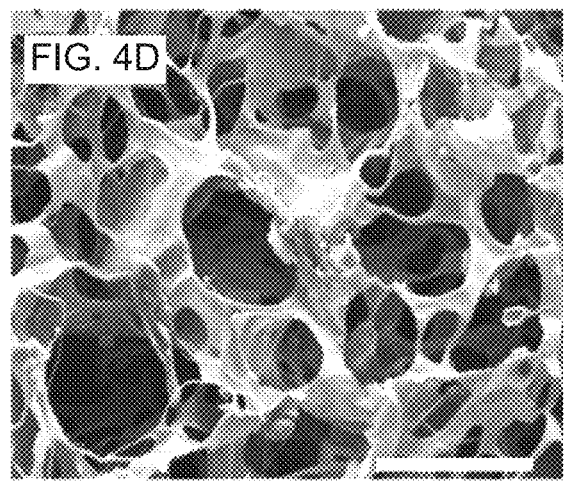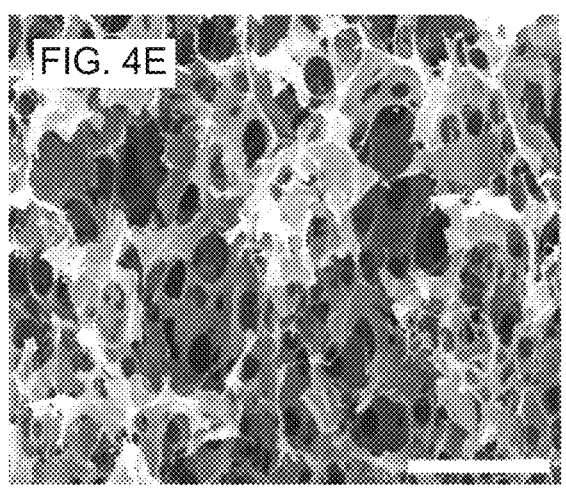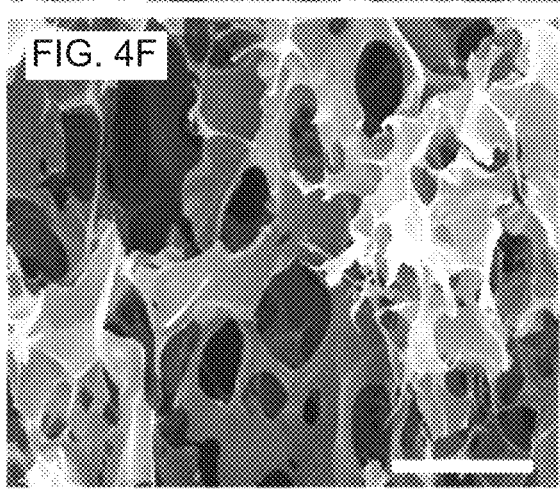

TISSUE STRUCTURE SCAFFOLDS

CROSS-REFERENCE TO RELATED APPLICATIONS

This application is a national stage entry from International Application No. PCT/EP2017/061542, filed May 12, 2017, and claims the benefit of prior application no. GB 1606976.7, filed Apr. 21, 2016, each of which is hereby incorporated herein by reference in its entirety.

BACKGROUND

This invention relates to a method of manufacture of collagen scaffolds, particularly but not exclusively tissue structure scaffolds, especially three dimensional (3D) porous cross-linked collagen or collagen-chitosan scaffolds which may be used for tissue engineering applications. The invention also relates to tissue scaffolds made by the method and to devices incorporating the scaffolds.

Tissue scaffolds find application in tissue engineering for improvement of tissue and organ repair and replacement of biological functions. Key components of tissue engineering are biomaterials that provide an interface similar to a naturally occurring extracellular matrix (ECM). This allows cells to grow on the material without being recognized as foreign to the body. Biomaterials have been based on biopolymers, especially based on biopolymers derived from the ECM.

Collagen, which is a natural biopolymer, is used in the biomedical industry for applications such as encapsulation, microspheres and matrices for implants and tissue engineering. Chitosan is also useful for biomedical and clinical applications because it has high biocompatibility, biodegradability and nonantigenicity. Chitosan-collagen hybrid polymer network scaffolds have been prepared by freeze-drying and have been evaluated using buffalo stem cells and with respect to growth of hepatic tissue.

Nanofibrous collagen (NF-collagen) mats have been prepared by using an electrospinning technique. (Ko C-L, Tien Y-C, Wang J-C, Chen W-C. *Characterization of controlled highly porous hyaluronan/collagen cross-linking sponges for tissue engineering. J Mech Behav Biomed Mater* 2012; 14: 227-38). The electrospinning technique typically forms two-dimensional collagen sheets and is incapable of fabricating 3D NF-collagen scaffolds with well-defined pore size. In order to facilitate effective tissue engineering, we recognized that the development of 3D porous structures is critical to the function of biological tissue, transport of oxygen and nutrients.

SUMMARY OF THE INVENTION

According to a first aspect of the present invention, a method of forming a scaffold comprises the steps of:
preparing a high internal phase emulsion (HIPE) comprising an aqueous solution of:
proteins selected from the group consisting of collagen and mixtures of collagen and chitosan; and
a cross-linking agent;
by addition of an immiscible solvent to the solution to form the HIPE;
reducing the temperature of the HIPE to solidify the HIPE;
removing water and solvent by vaporisation at a temperature above the melting point of the solvent to form a porous structure; and
before or after removal of solvent, causing cross-linking of the protein with the cross-linking agent to form a cross-linked scaffold structure.

The invention is further described by means of example but not in any limitative sense with reference to the drawings, of which:

BRIEF DESCRIPTION OF THE DRAWINGS

FIG. 1 shows the internal structure of non cross-linked collagen polyHIPES;

FIG. 3 shows the internal structure of freeze dried glutaraldehyde cross-linked collagen polyHIPES;

FIG. 4 shows the internal structure of air-dried collagen polyHIPES (10% ww) crosslinked with glutaraldehyde;

DETAILED DESCRIPTION

The collagen structure of the present invention may have fundamentally the same chemical composition as natural collagen and may be used for guiding tissue regeneration. Particularly advantageous embodiments have the advantage that they exhibit the nanofibrous architecture which is beneficial to regulation of cell adhesion and function.

Collagen gels form through a single-strand-to-triple helix transition. However, chemical cross-linking is a much more consistent method to ensure structural integrity and to provide a gel which exhibits an optimized, reproducible performance in vivo or under physiological conditions.

The method may be used to induce tissue formation from liver cells, skin fibroblast cells, bone cells, cartilage or skin cells.

According to a second aspect of the present invention, a three-dimensional tissue scaffold structure comprises: a protein selected from the group consisting of: collagen and mixtures of collagen and chitosan, cross-linked with a cross-linking agent.

The term "scaffold" used in the present invention refers to a three-dimensional structure with a porous microstructure suitable to support cells during tissue growth.

Preferred scaffolds in accordance with this invention have beneficial configuration, morphology and properties suitable for tissue engineering including: good biocompatibility, mechanical performance, a degradation rate which can match a rate of tissue regeneration and a highly porous interconnecting structure. Use of cell lines which are difficult to grow by other methods is facilitated.

The scaffold may have the structure of a collagen foam with a porous structure suitable for use as a tissue scaffold.

Embodiments of the invention comprising a scaffold formed from crosslinked collagen, chitosan or mixtures thereof may have particular suitability for use in comparison to previously disclosed porous polymers, for example polystyrene based poly-HIPE structures.

The tissue scaffold of the present invention may comprise voids interconnected by pores. The scaffold may include struts extending between adjacent pores or voids, the struts each having a length and thickness.

The structure of a scaffold of this invention may be characterised by one or more of the following properties:

1. Structure of the Scaffold—

(a) Shape and Configuration of the Voids

Figure 2A:
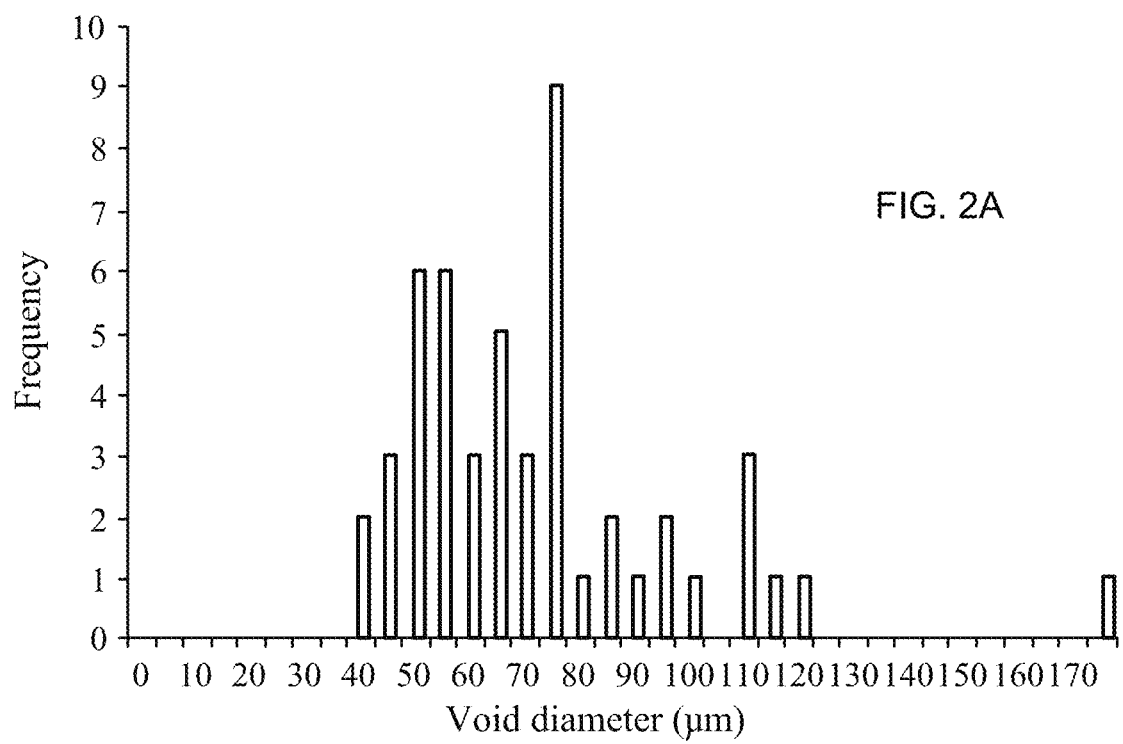
FIG. 2 shows the void sized distribution of air-dried polyHIPE materials.
Figure 2B:
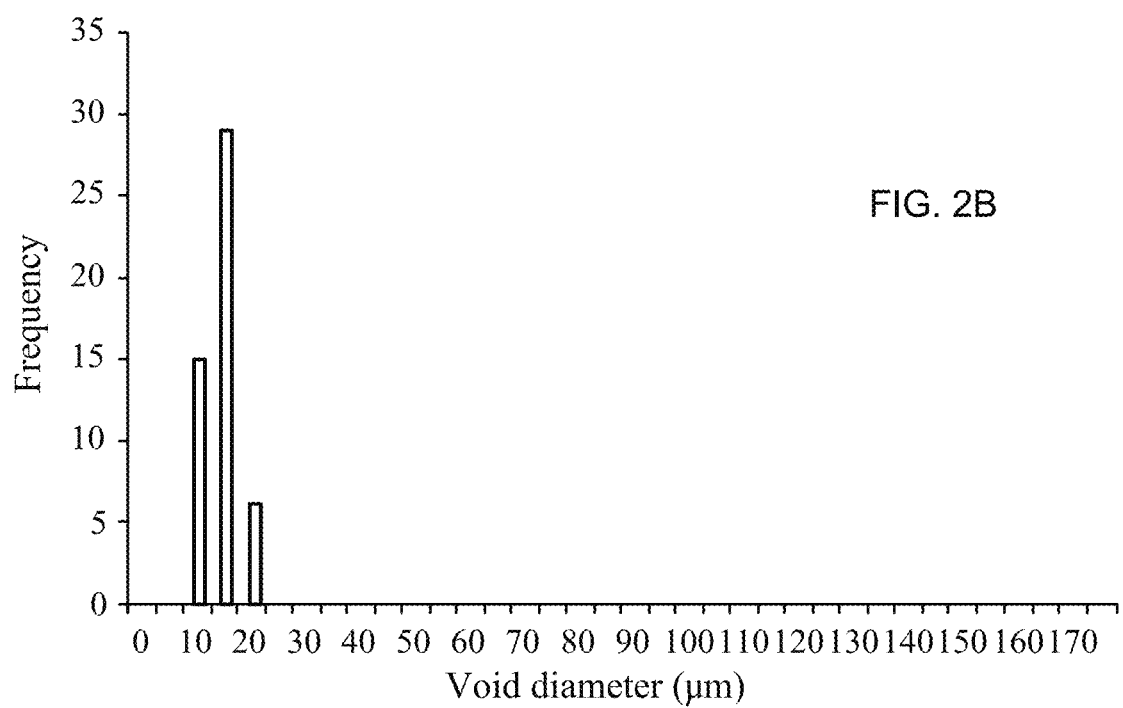
Figure 2C:
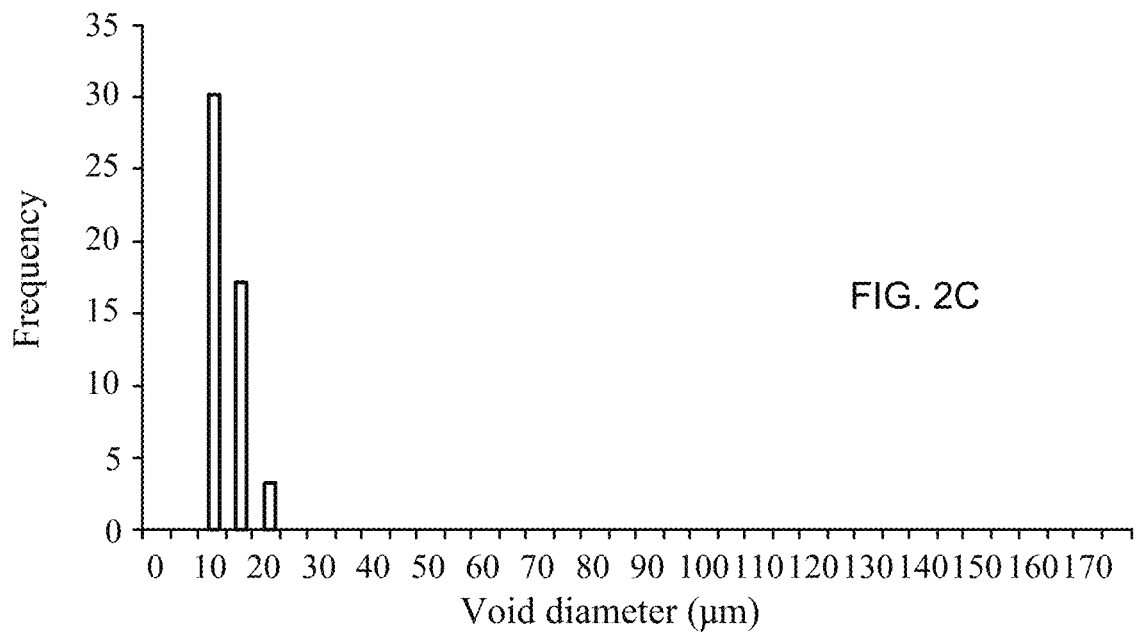
Figure 2D:
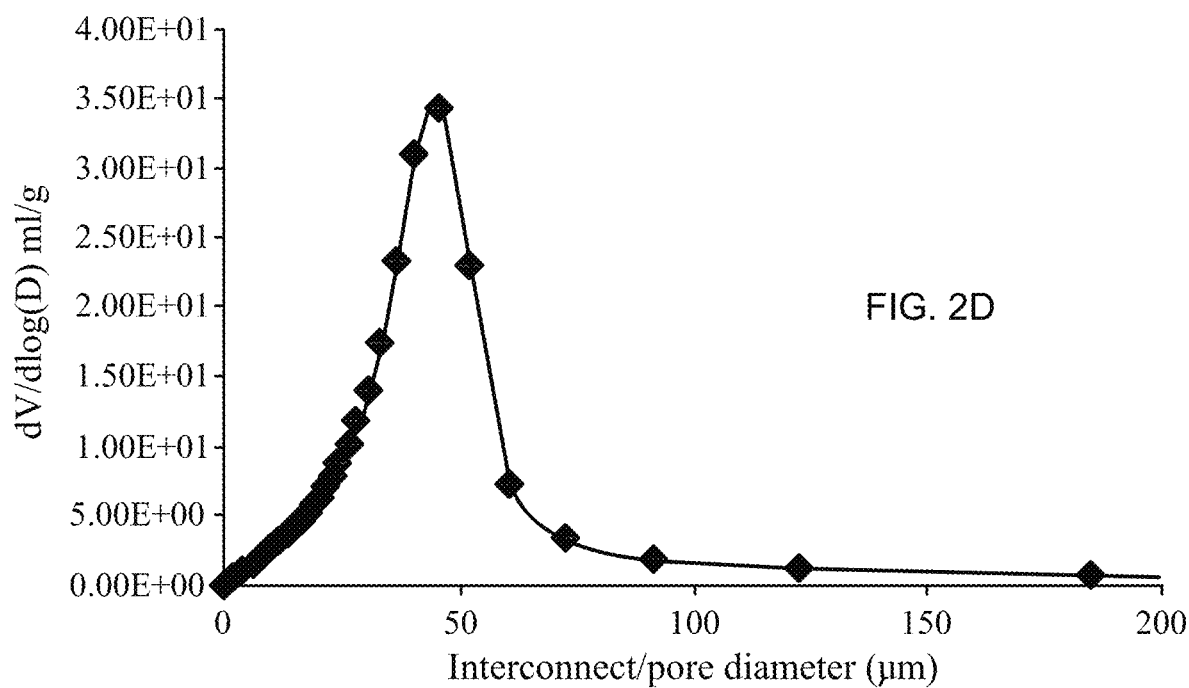
Figure 5:
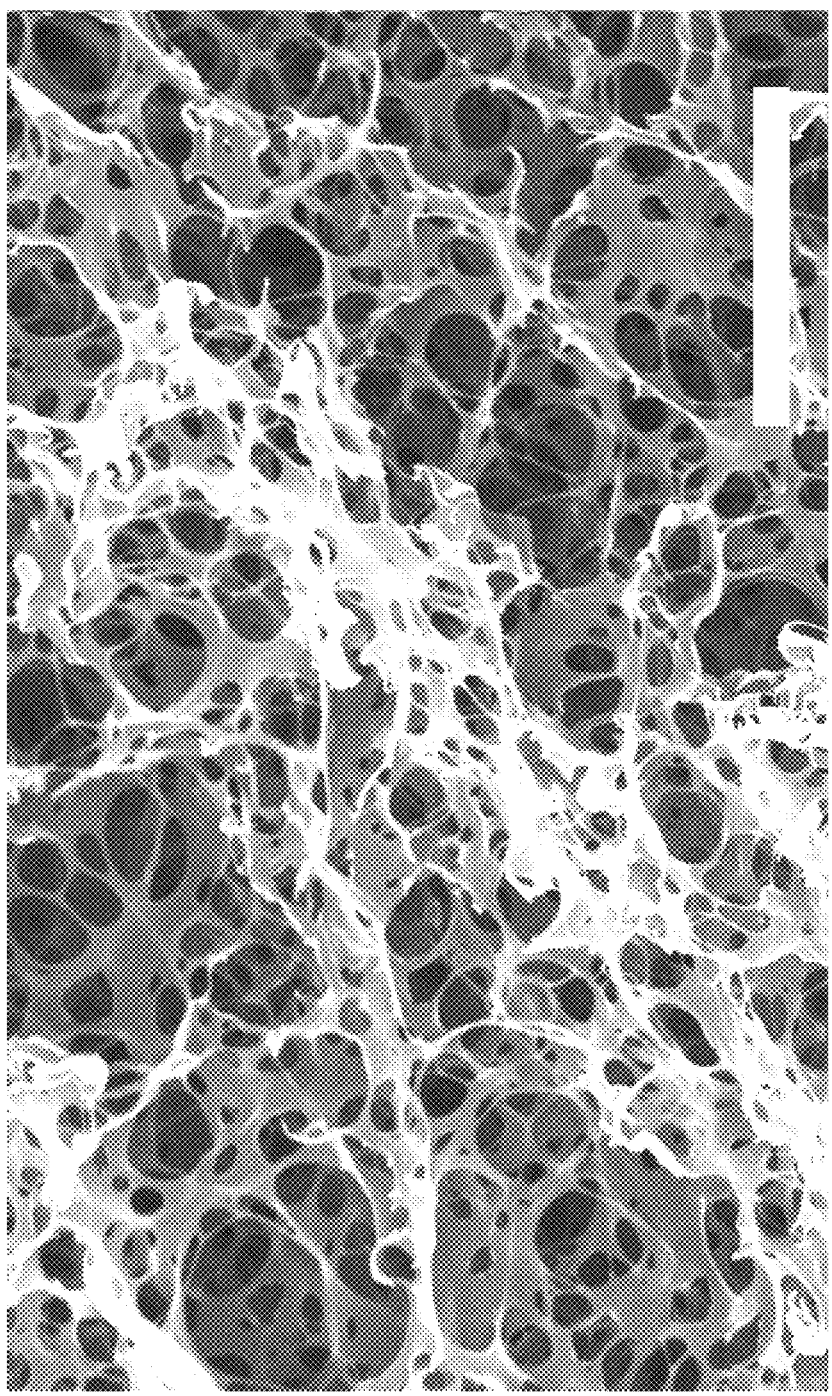
FIG. 5 shows scanning electron microscope images of the internal structure of collagen-chitosan polyHIPE materials.

Embodiments of the invention allow manufacture of a scaffold with a configuration and properties which closely resembles decellularised natural tissue, for example rat liver tissue (Uygun et al; *Nature Medicine* 2010, 16, 814-821. See FIG. 2g on page 816).

Previously disclosed poly-HIPE structures have a high proportion of spherical or near-spherical voids with circular or near-circular pores. A low interconnect pore sized distribution was described in Carnachan, R. J.; Bokhari, M; Przyborski, S. A. and Cameron, N. R.; *Soft Matter* 2006, 2, 608-616. See Table 1 and FIG. 4. In such prior art arrangements the voids are generally spherical.

Scaffolds of the present invention may have a substantial absence of spherical voids. The struts between adjacent pores may have a wide range of thicknesses and lengths in comparison to poly-HIPE structures, as disclosed in Carnachan et al. Less than 10% of the voids may be spheroidal or approximately spherical. Preferably there are no spheroidal or approximately spherical voids.

(b) Shape and Size Distribution of the Pores Interconnecting Adjacent Voids—

Embodiments of the invention allow manufacture of scaffolds with configurations and properties which closely resemble decellularised natural tissue, for example rat liver tissue.

Previously disclosed poly-HIPE structures have a high proportion of spherical or near-spherical voids with circular or near-circular pores. A low interconnect pore size distribution was observed, as illustrated in Carnachan, et al.

In such prior art arrangements the voids are generally spherical, typically having a mean void size of 94 µm and a range of pore sizes from 10 to 30 µm and a mean pore size of 19 µm. This is a narrow pore size distribution.

Scaffolds of the present invention may have a substantial absence of spherical or spheroidal voids. The struts between adjacent pores may have a wide range of thicknesses and lengths in comparison to poly-HIPE structures.

Embodiments of the invention may provide a high variety of configurations or shapes of the voids and pores. The voids may be dimensioned so that 90% of the voids have a mean size in the range 3.5 µm to 6.5 µm. The voids may typically have a mean size of 4.5 µm and a standard deviation of ±1.8 µm. The corresponding structure of rat liver tissue may have a void size of 4.2 µm±2.2 µm. The pore size may be in the range 2.0 µm to 8.7 µm, comparable to the pore size of rat liver which may be 1.0 µm to 12 µm.

(c) Uniformity of Configuration of the Voids and Pores—

In embodiments the uniformity of the dimensions and configurations of the voids and pores are low. The boundaries between adjacent voids or pores may be irregular with a substantial absence of spherical voids and circular shaped pores.

(d) Aspect Ratio of the Dimensions of the Pores—

The aspect ratio of the pores may be defined by the ratio of the minimum dimension (dmin) to the maximum dimension (dmax). These may be measured on perpendicular axes or otherwise angled axes. With non-circular pores the minimum and maximum dimensions are not perpendicular. In embodiments the aspect ratio, dmin/dmax, 50% of the pores may be less than about 0.7, alternatively 50% less than about 0.5, alternatively 50% less than about 0.4.

In contrast, a prior art poly-HIPE structure may have 50% of voids with an aspect ratio greater than 0.7, commonly greater than 0.8, typically greater than 0.9.

2. Surface Area of the Scaffold Defining the Voids

Scaffolds of the invention may have laminar regions in the form of webs between the pores. This configuration provides a relatively high surface area of the voids of the scaffold. A high surface area may be beneficial to cell growth, particularly in combination with a high degree of interconnection by pores between the voids.

3. Softness of the Scaffold.

Scaffolds of the invention may include laminar regions in the form of webs between adjacent pores. This configuration provides a relatively high surface area of the scaffold defining the voids. A high surface area may be beneficial to cell growth, particularly in combination with a high degree of interconnection by pores between the voids.

The softness or conversely stiffness of the scaffolds may be determined as the gradient of stress-strain behaviour for the scaffold.

In embodiments the stiffness of the scaffold is similar to soft tissues such as liver, for example within 30%, alternatively within 20%, further alternatively within 10%, of the value for liver tissue. The stiffness may be determined by manual inspection or may be measured instrumentally.

An important property is that the scaffold may have a softness selected to be similar to that of natural collagen to facilitate cellular expression, for example of liver cells. The stiffness or softness may be controlled to have a value close to that of an alternative tissue type, as required.

In preferred embodiments, the scaffold of the present invention may exhibit one or more of the following properties. The scaffold comprises interconnected pores. The porosity may be greater than 70%, alternatively greater than 80%, alternatively greater than 90%, for example 91% as measured by mercury porosimetry.

The scaffold of the present invention may find application in making repair tissue which resembles natural tissues, but without having a biological history, for example dependent on age, disease, gender or environmental factors. Consistency of tissue characteristics can be controlled.

Advantageous embodiments of this invention have a microfibrous structure, particularly with a thin interconnecting strut dimension. For example the structure may have struts with a length in the range 0.5 µm to 6 µm, preferably 0.6 µm to 5.5 µm. The struts may have an average thickness of 1 to 3 µm, preferably 1 to 2 µm. A microfibrous structure is particularly effective in regulating cell adhesion to the scaffold.

The cross-linking step may take place before or after complete or partial removal of the solvent.

Cross-linking may be taken to completion before removal of the solvent. Alternatively, cross-linking may be carried out on the solidified solvent-free structure. Alternatively, an initial partial cross-linking step may be followed by solvent removal and a further cross-linking step.

A preferred cross-linking agent is glutaraldehyde (GA).

Of the cross-linking agents which may be employed are genipin, carbodiimide, transglutaminase, chondroitin sulphate, dextran dialdehyde, bis(vinylsulfonyl)methane and hexamethylene di-isocyanate.

The concentration of the cross-linking agent, preferably glutaraldehyde, in the emulsion may in the range of 1 wt % to 5 wt %, preferably 2 wt % to 3 wt %, more preferably about 2.5 wt %. The concentration of the cross-linking agent may be selected to provide a desired degree of stiffness or softness dependent on the required properties of the tissue scaffold.

Using glutaraldehyde as a cross-linker in accordance with this invention does not require use of vinyl derivatives of collagen and allows for quicker production of collagen based porous materials removing the need for purification of any vinylised derivatives.

Polymerisation of a high internal phase emulsion (HIPE) template produces a material (referred to as a PolyHIPE) with an internal pore structure which can be controlled by varying one or more manufacturing conditions such as emulsion stability, stirring rate and rate of droplet phase addition. For polymeric foams such as those based on styrene/DVB water-in-oil, HIPEs have been used as templates prior to polymerisation. When using a water soluble polymer such as collagen, an inverse oil-in-water HIPE may be formed. The porous structure is produced either on cooling below the gelation temperature or by the addition of a cross-linking agent.

The concentration of collagen in the emulsion may in the range of about 5 wt % to about 30 wt %, preferably about 7.5 wt % to about 15 wt %. Relatively high concentrations of collagen have been found to reduce swelling of the scaffold on contact with water, providing a more stable scaffold structure.

The aqueous solution may further comprise a surfactant, for example in an amount of 5 wt % to 10 wt %, typically about 7 wt %. An amphoteric surfactant is preferred, for example disodium cocoampho dipropionate, for example manufactured by Solvay under the trade mark MIRANOL C2M-SF Conc. An alternative non-ionic surfactant is octylphenol ethoxylate, for example manufactured by the Dow Chemical Company under the trade mark TRITON X-405.

The HIPE may be solidified by freezing, for example by cryogenic freezing. Use of a controlled freezing rate is not necessary in carrying out the method of the present invention. Freeze drying may be employed to remove the water and organic solvent. For example, if the solvent is toluene (melting point −90° C.) the emulsion may be frozen to a temperature of about −80° C. so that the solvent can be removed by evaporation.

The organic solvent may be added over a period of 2 minutes at a rate dependent on the size of the sample to be prepared.

According to a third aspect of the present invention, there is provided a prosthetic scaffold in accordance with the second aspect of this invention. The scaffold may have a three-dimensional structure suitable for manufacture of a prosthesis. For example, a nerve prosthesis may be made using a tubular structure. A thin sheet structure may be used for making an ocular prosthesis. A sheet or block structure may be used for making a liver tissue. A laminar or foldable structure may be used for making bone prostheses. The three-dimensional structure may be selectively configured to conform to the dimensions of a lesion to facilitate lesion repair.

2. Materials and Methods

The following materials and methods were used 2.1 Materials

Collagen, glutaraldehyde (GA) (25% w/v in water), dexamethasone, β glycerphosphate disodium salt hydrate and 2-phospho-L-ascorbic acid trisodium salt were obtained from Sigma-Aldrich. Dulbecccos Modified Eagles medium (DMEM), phosphate buffered saline (PBS), penicillin/streptomycin and trypsin/EDTA were obtained from Life Technologies 2.2. Preparation of Collagen PolyHIPEs The apparatus for the HIPE preparation consisted of a three-necked round bottom flask filled with a D-shaped paddle driven by an overhead stirrer. Collagen was dissolved in deionised water containing 7% Miranol C2M-CONC as surfactant. The flask, containing the collagen solution, was only partially submerged in the water bath maintained at 50° C. This is the temperature at which concentrated collagen solutions are suitable for processing into a HIPE. Toluene was then added dropwise to achieve a 3:1 ratio (15:5 ml or 45:15 ml). By the end point a white HIPE had formed. The HIPE was stirred for a further 5 minutes and then transferred to a 50 ml Polyethylene bottle or centrifuge tube. Glutaraldehyde (GA) (2.5% w/v in water) was then added and mixed into the HIPE by gentle shaking. The HIPE was then allowed to gel overnight prior to washing in ethanol and deionised water to remove the toluene and surfactant respectively. The washed materials were then frozen in liquid nitrogen and freeze dried for 24-48 hours.

Collagen PolyHIPEs (GA cross-linked) were then placed in 12-well culture plates and washed in 0.1 M glycine overnight to inactivate vacant aldehyde groups. The materials were then sterilised with 70% ethanol for 30 minutes, then washed with phosphate buffered saline three times. The materials were finally washed with Soas-2 culture medium (2-3 ml) and maintained at 37° C. and 5% $CO_2$ until cell inoculation.

For non-cross-linked collagen materials, samples were placed in 12 well plates and post cross-linked in 2 ml of 2.5% w/v GA overnight. The cross-linked samples are then washed in PBS (×5) to remove the residual GA and soaked in 2 ml of 0.1M glycine solution for 4 hours to deactivate vacant aldehyde groups. The samples are then sterilised in 70% ethanol and washed with PBS (×3) and then finally washed in 2-3 ml of Saos-2 culture medium prior to cell inoculation.

2.3. Preparation of Collagen-Chitosan PolyHIPEs

The preparation followed was essentially that given in section 2.2. For collagen-chitosan composite materials, collagen (1.5 g, 10% w/w) and chitosan (0.3 g, 2% w/w) were dissolved in 2% acetic acid containing Miranol C2M-CONC. The solution was maintained at 50° C. and toluene was added dropwise to the solution until a HIPE had formed. These materials were then cross-linked and processed as described above for the collagen materials.

2.4. Saos-2 Cell Culture

For standard cell culture, Saos-2 cells are maintained in DMEM (Gibco, Life Technologies) containing 10% FBS (Gibco, Life Technologies) and 100 U/ml Penicillin/Streptomycin (Gibco, Life Technologies).

2.5. 3D Cell Culture i) Saos-2 cells were seeded at 250,000 cells per scaffold in 12 well plates. Saos-2 cells were maintained in osteogenic differentiation media, DMEM supplemented with 10% FBS, 10 nM dexamethasone, 5 mmol/l β glycerophosphate and 100 μg/ml ascorbic acid. Cells were allowed to settle for 30 minutes after seeding prior to flooding the well with 3 ml of differentiation media.

ii) L929 cells were seeded at 100,000 cells/50 μl per well ($2\times10^6$ cells/ml) and allowed to settle on the scaffolds for 30 minutes in the cell incubator. The wells were then topped up with 3 ml of culture media and placed by in the incubator and maintained at 37° C. and 5% $CO_2$. L929 cells were culture on the natural collagen scaffolds for 10 days.

iii) Three primary human cell types (i.e. primary human hepatocytes (PHH), human liver cancer cell line HepG2 and primary human hepatic stellate cells) were cultured on the natural collagen scaffolds made as described in the present invention (N type). Also they were compared with relatively soft styrene-EHA (2-ethylhexyl acrylate) 3D polyHIPE synthetic scaffolds (S type) and 2D hard plastic standard tissue culture plates. All cells cultured successfully. The natural collagen scaffolds (N type) promoted improved phenotypes compared to those on synthetic scaffolds (S type). In particular, primary human hepatic stellate cells cultured on the collagen scaffolds (N type) had reduced activation ("more in vivo like") compared to those cultured on traditional 2D hard plastic.

2.6. DNA Analysis

A freeze-thaw technique was used for cell lysis. Cultures were washed with biological grade water and placed in 1.5 ml falcon tubes containing 1 ml of biological grade water. Cells cultured in 2D were removed using a cell scraper and re-suspended in 1 ml of biological grade water. Cell lysates were stored at −20° C.

DNA content was analysed using the QUANT IT PICOGREEN assay (Life Technologies). Cell lysates were thawed at 37° C. and homogenised using a 21G needle (10-15 times), samples were then diluted 1 in 10 with TE buffer (1×) by placing 10 μl of sample and 90 μl of TE buffer in a black bottom 96-well plate. 100 μl of PICOGREEN reagent was then added and mixed at room temperature for 5 minutes whilst wrapped in tin foil. The fluorescence was then measured at excitation and emission wavelengths of 480 and 520 nm respectively.

2.7. Alkaline Phosphatase Activity

A freeze-thaw technique was used for cell lysis. Cultures were washed with biological grade water and placed in 1.5 ml falcon tubes containing 1 ml of biological grade water. Cells cultured in 2D were removed using a cell scraper and re-suspended in 0.5 ml of biological grade water. Cell lysates were stored at −20° C.

Alkaline phosphatase (ALP) levels are associated with various diseases in the liver and bone. The AbCam alkaline phosphatase kit uses p-nitrophenyl phosphate (p-NP) as a phosphate substrate which turns yellow (405 nm) when dephosphorylated by ALP.

Cell lysates were thawed at 37° C. Then 5 μl of cell lysate was added to each well of a 96-well plate. The volume was then made up to 80 μl using the assay buffer. 50 μl of p-NP (5 mM) was then added to each sample well. The plate was then wrapped in tin foil and incubated at room temperature for 60 minutes. The absorbance was then read at 405 nm using a Synergy H4 plate reader. The sample readings were then applied to the p-NP standard curve and ALP activity of the test samples calculated as follows:

$$\text{ALP activity (U/ml)} = A/(V*T) \tag{1}$$

where:

A is amount of p-NP generated by samples (μmol).
V is the volume of sample added in the assay well (in ml)
T is the reaction (in minutes).

ALP activity was then normalised to DNA content of the samples to give activity in Units per ng DNA.

2.8. Determination of Internal Structure and Pore Size

The median pore size of the material was determined using Mercury Intrusion Porosimetry which was performed using a Micromeritics AutoPore IV. Intrusion and extrusion mercury contact angles of 130 degrees were used. The penetrometers had a stem volume of 1.836 ml and bulb volume of 5 ml. Void diameter ranges were investigated using Scanning Electron Microscopy (SEM, Philips XL30 SEM) operating at 15 kV. Prior to visualisation, fractured samples were coated with gold and mounted onto aluminium stubs using carbon pads. Void diameter sizes were calculated as described previously.

2.9. Histology and Immunohistochemical Analysis

Samples were washed 3 times in PBS and then fixed in 4% PFA overnight. Samples were then dehydrated through a series of graded ethanol (40, 60, 80, 90 and 95% ethanol) for 1 hour and then in 100% ethanol for 1 hour, histoclear (15 minutes), 50/50 histoclear/wax (30 minutes) and 100% wax (60 minutes). The samples were then transversely embedded into moulding cassettes and left to cool overnight. Sections of 10 μm were then dewaxed and rehydrated through a series of graded ethanol. The sections were then incubated with permeabilisation solution and blocking buffer (15 minutes each solution). For antibody staining, sections were incubated with the primary osteocalcin antibody overnight in a humidified chamber. After primary incubation the sections were then washed and incubated with the appropriate secondary antibody for 60 minutes in the dark. The sections were then mounted in coverslips using DAPI/Vectashield. For standard Haematoxylin and Eosin staining the sections are left in Haematoxlyin and Eosin respectively to visualise cell nuclei and staining of the collagen material structure. Sections were visualised using Leica DM500 and DMI 300 B microscopes.

2.10. Swelling Studies

Dry samples were weighed and placed in centrifuge tubes containing 30 ml of water. The samples were then removed after 30 minutes. The excess water was removed using a dry paper towel and the swollen samples were then reweighed and placed back into 30 ml of water. This process was repeated every 30 minutes for up to 120 minutes. The swelling ratios ($W_{SR}$) of the materials were calculated using equation 3.

$$W_{SR} = (W_t - W_0)/W_0 \tag{3}$$

$W_t$ represented the weight of the wet scaffolds and $W_0$ represented the initial weight of the dry scaffolds.

3. Results 3.1. Experimental Procedures

Collagen HIPEs were prepared initially using two different surfactants. However those prepared using Triton X-405 were not as stable as those prepared using Miranol C2M-CONC, especially at the 60 ml emulsion scale. Only those made using Miranol CM-SF CONC are referred to below. After the addition of the cross-linker glutaraldehyde the gelation occurs rapidly. The gelated HIPEs were orange in colour with the resulting freeze dried monolith being a slightly paler orange colour. The ratios of cross-linker used for gelation at a 20 ml scale for 10% w/w collagen concentration are shown in Table 1. For varying concentrations of collagen and for 60 ml production, the amounts were adjusted accordingly.

TABLE 1

Cross-linking ratios for materials containing 10% w/w collagen

| Collagen (g) | Glutaraldehyde (2.5% v/v) (mL) | Cross-linking ratio (% w/w) |
|---|---|---|
| 0.5 | 0.25 | 0.125 |
| 0.5 | 0.5 | 0.25 |
| 0.5 | 1 | 0.5 |
| 0.5 | 2 | 1 |

3.2 Structural Analysis

The internal pore structure of the collagen materials was analysed using Scanning Electron Microscopy.

All of the collagen air dried PolyHIPE materials exhibited the standard PolyHIPE emulsion templated structure. All of the materials exhibited an open interconnecting structure with void size decreasing with increasing collagen concentration (FIG. 1). The increase in HIPE viscosity with increasing collagen concentration correlates with increasing emulsion stability.

The void size of the template material is controlled by the emulsion droplet size, and this can be regulated by affecting the emulsion stability by varying temperature and time of the droplet phase. The interconnecting windows/pores are also controlled by the emulsion stability and are formed during polymerisation of the continuous phase film surrounding the emulsion droplets. At the higher concentration of collagen it becomes more difficult to observe a well-defined void structure (FIG. 1E-F).

From image analysis of the collagen PHP materials, increasing the collagen concentration leads to a material with a narrower range of void sizes and a smaller overall average void size of the material (FIG. 1A-C.). The void size reduces from 70 μm to 10 μm as one progresses from 10% and 30% collagen. This is due to the increase in emulsion viscosity with increasing collagen concentration suggesting an increase in HIPE stability as the concentration of collagen increases. Increased HIPE stability leads to a porous material with smaller average void size as discussed in the literature.

Increasing the concentration of collagen to 20% w/w produced a PHP material with lower porosity with thicker strut size compared to nanofibrous structure observed with the 10% w/w collagen material.

Figure 8:
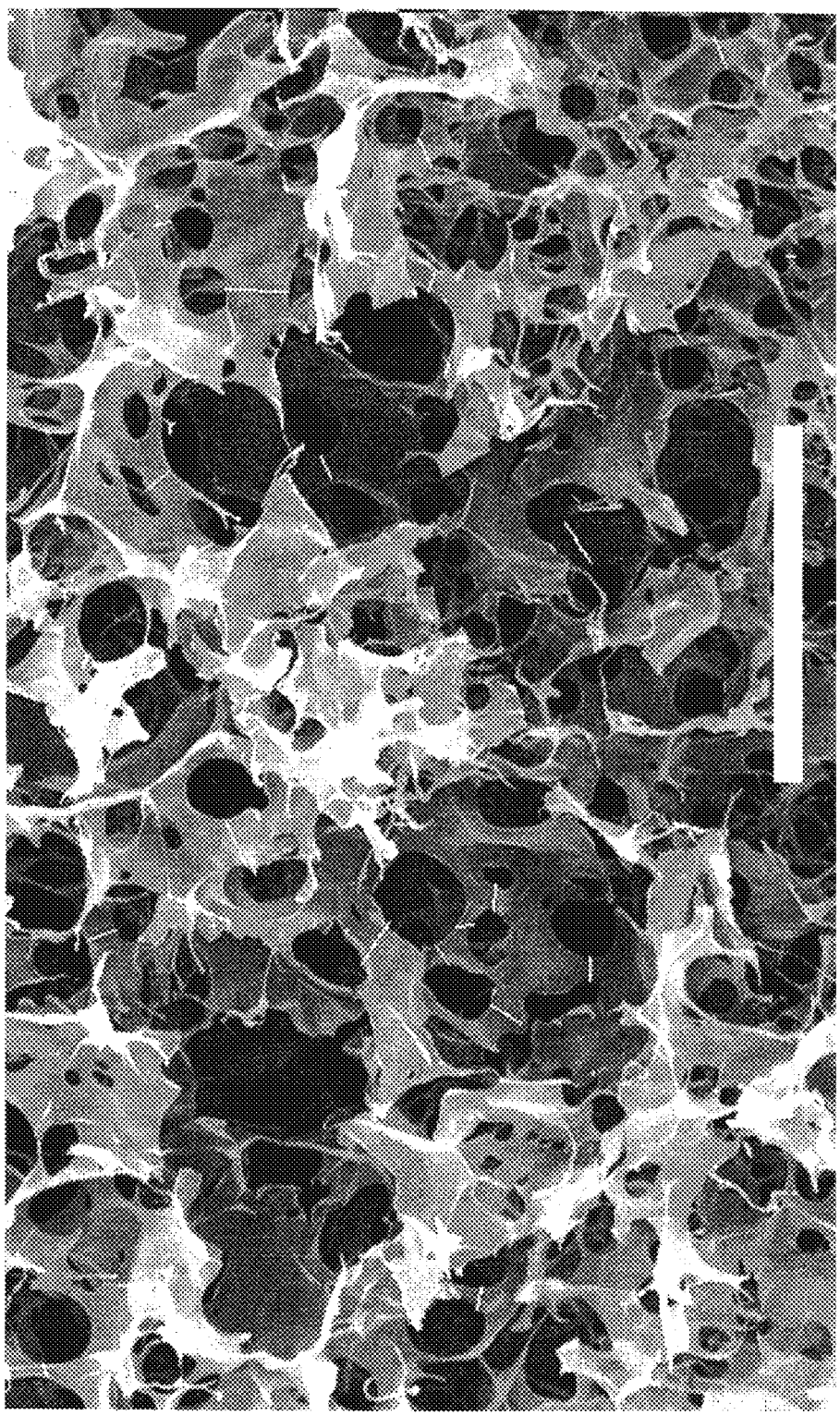
FIG. 8 shows a scanning electron microscope (SEM) image showing the internal structure of air dried collagen polyHIPE (10 wt %) cross-linked with glutaraldehyde with strut dimensions labelled.

Freeze-dried collagen PolyHIPEs (GA cross-linked) again exhibited a highly interconnected porous structure (FIG. 3.). No defined spherical void structure could be observed from SEM images and mercury intrusion porosimetry calculated a median interconnect diameter of 39 μm (FIG. 1D.), indicating an extremely open interconnecting structure. The GA cross-linked materials exhibited more of a nanofibrous structure compared to the non cross-linked materials. Two different methods were used to crosslink the materials; the GA was added either added to the HIPE directly after HIPE formation, or to the dried materials which were post cross-linked in GA solution overnight. The air dried GA cross-linked materials exhibited a more uniform interconnecting structure compared to the freeze dried materials (FIG. 4.) The strut dimensions of the structure are marked as white bars on the photomicrograph shown in FIG. 8.

3.3. Collagen-Chitosan PolyHIPE

The internal structure of air-dried collagen-chitosan polyHIPE cross-linked with glutaraldehyde was shown to indicate successful cell culture.

3.4 DNA Analysis and Alkaline Phosphatase Activity (ALP).

Figure 6:
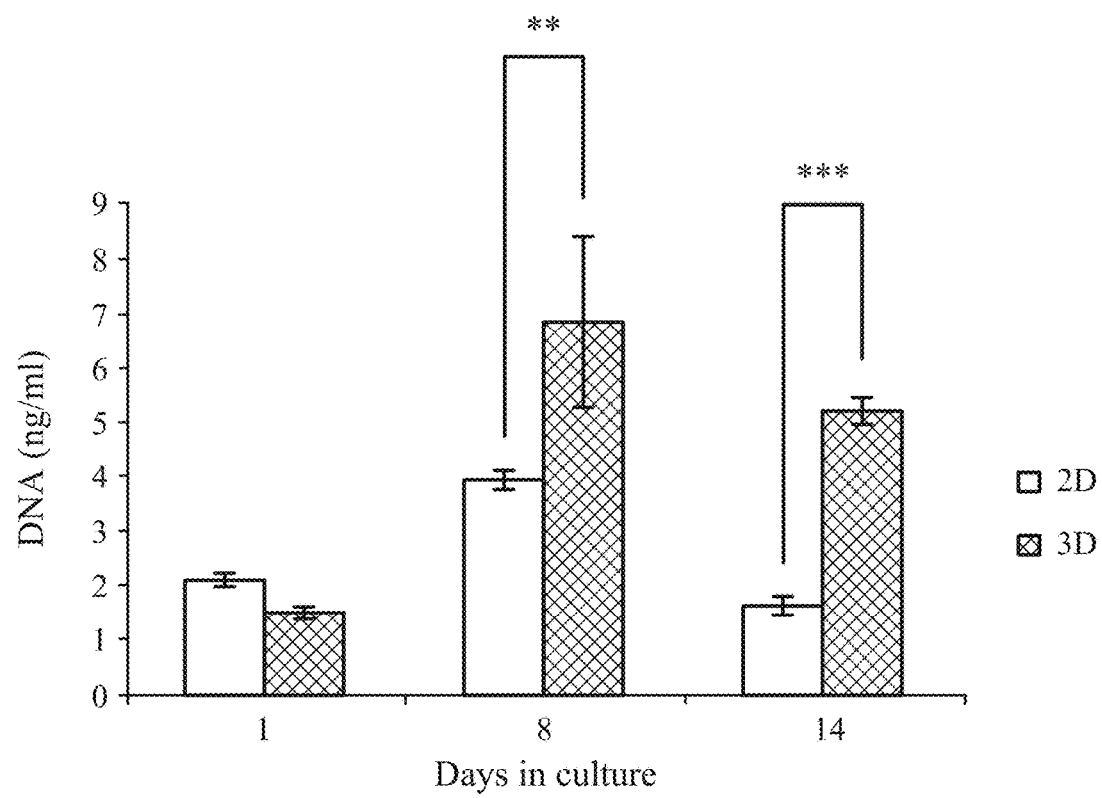
FIG. 6 shows the DNA content of Soas-2 cultures in collagen based polyHIPES.
Figure 7:
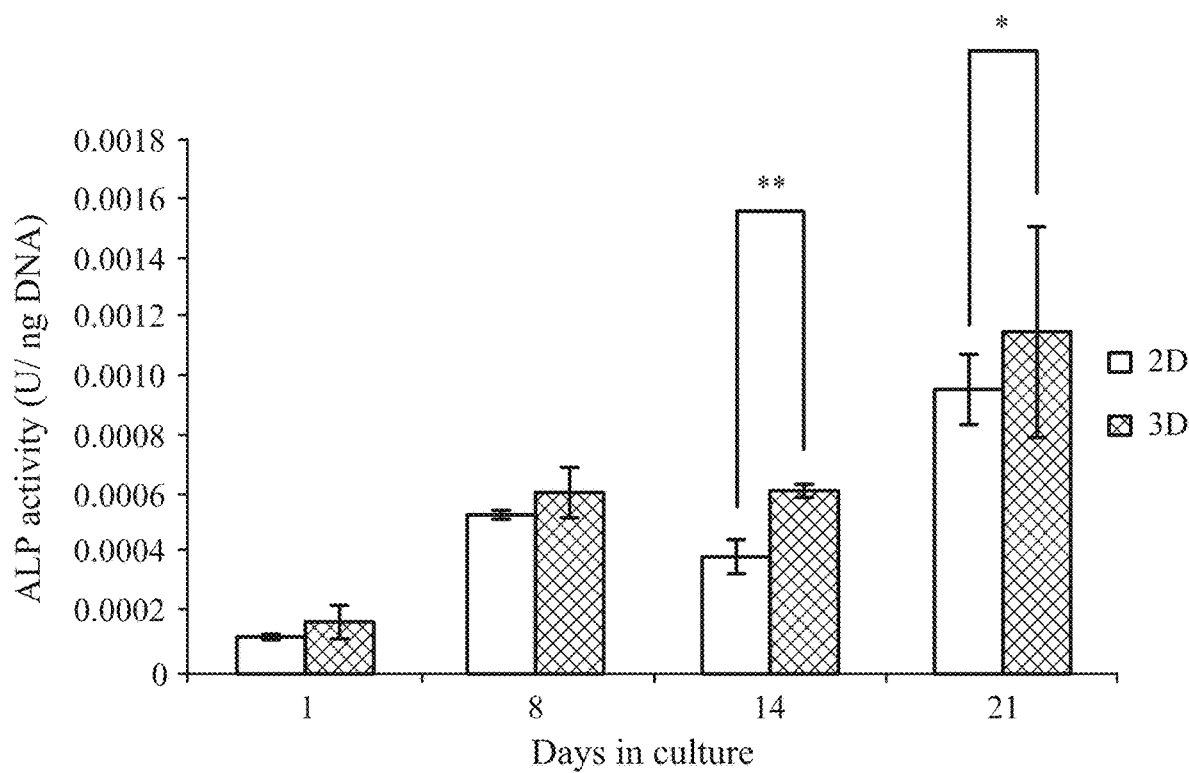
FIG. 7 shows swelling ratio of non cross-linked collagen materials and collagen materials cross-linked with glutaraldehyde.

DNA analysis was used to study cell growth/number on both of 2D and 3D culture of Saos-2 cells. Increased levels of DNA were observed in the 3D collagen scaffolds compared to 2D after the first 24 hours of culture (FIG. 6.). The levels were highest after 8 days on both the 3D and 2D cultures. After 14 days, cell growth levels decrease in both the 2D and 3D cultures possibly due to cell differentiation. At 21 and 35 days increased levels were observed in the 3D collagen cultures compared to standard 2D cultures (data not shown).

Alkaline phosphatase (ALP) catalyses the hydrolysis of phosphate esters in alkaline buffer and produces an organic radical and inorganic phosphate. Changes in alkaline phosphatase level and activity are associated with various diseases state in liver and bone. Alkaline phosphatase is involved in the maturation step of osteoblasts during differentiation. This enzyme belongs to a family of proteins that are anchored to the plasma membrane via a glycosyl-phosphatidinositol linkage. ALP is one of the earliest phenotypic markers for a committed osteoblast. In general, committed osteoblasts exhibit higher basal levels of ALP than do cells which do not mineralise their matrix, such as fibroblasts. The expression of ALP mRNA and enzyme activity before the initiation of osteoblast mineralization suggests that alkaline phosphatase may be involved in preparing the extracellular matrix for the deposition of mineral and for the co-expression of other genes. High levels of ALP are seen in both pre-osteoblasts and osteoblasts in vivo and in differentiating osteoblasts in vitro. The biological functions of ALP is still unknown except for its role in bone mineralization. Connective tissue cells expressing high levels of ALP can be induced to deposit mineral in vitro. ALP may be involved in the degradation of inorganic pyrophosphate, thereby providing a sufficient local concentration of phosphate or inorganic pyrophosphate for mineralization to proceed. Studies have been carried out to show how vital ALP is for bone formation. In a human model of ALP deficiency, hypophosphatasia, the bone became soft in the absence of ALP activity, suggesting that ALP physiological function is to maintain bone mineralization after birth. More recently two mouse ALP knockout models showed that, when the gene for ALP is specifically deleted, the mice develop defects in bone mineralization shortly after birth but not necessarily during embryonic development. Unknown redundant or backup mechanisms may provide for mineralization during embryonic life in ALP-deficient knockouts, so that ALP might still play an important role in the initial mineralization processes in bone. These results suggest that ALP may play an important role in the maintenance of bone mineralization.

The ALP activity after normalisation to DNA content, showed increased ALP levels per cell after 14 and 21 days on the 3D collagen materials compared to standard 2D culture. The 3D collagen porous materials provide a suitable biomimetic environment for enhanced differentiation of bone cells. (Data for 35 days not shown.)

3.5 Histological Analysis

Haematoxylin staining of cell nuclei showed the presence of Soas-2 cells (24 hours growing within the top third of collagen matrix. However the collagen scaffolds also showed a strong pink/red colour when stained with Eosin, which made deciphering between cells and scaffold difficult when used in combination.

Further DAPI staining of cell nuclei indicated Saos-2 cells penetrating into the collagen scaffold structure showing good 3D cell growth after a further 7 days in culture. Osteocalcin is a late marker for bone differentiation. Collagen-based PolyHIPE materials reported in the literature have been manufactured from vinyl derivatives of collagen, chondroitin sulfate and hyaluronic acid; to allow for free radical polymerisation of the collagen.

Figure 9A:
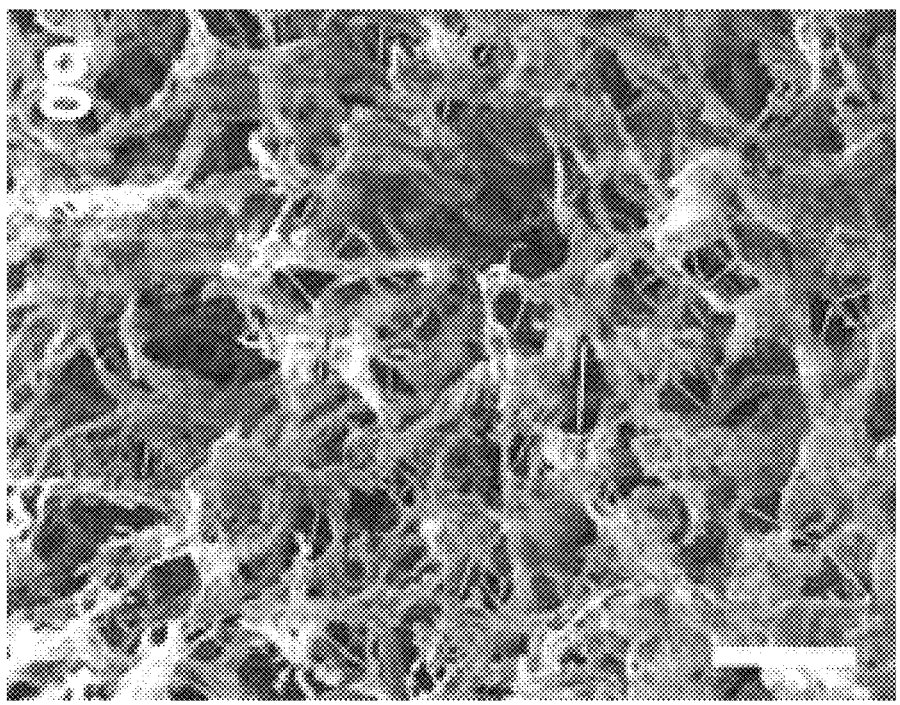
FIG. 9a is a SEM micrograph of decellularised liver.

FIG. 9a is a SEM micrograph of decellularised liver tissue (Uygun et al; Nature Medicine 2010, 16, 814-821). Size of interconnecting pores were assessed using the added measurement bars, some of which are indicated by the fine lines in the micrograph. Scale bar represents 20 micron.

Figure 9B:
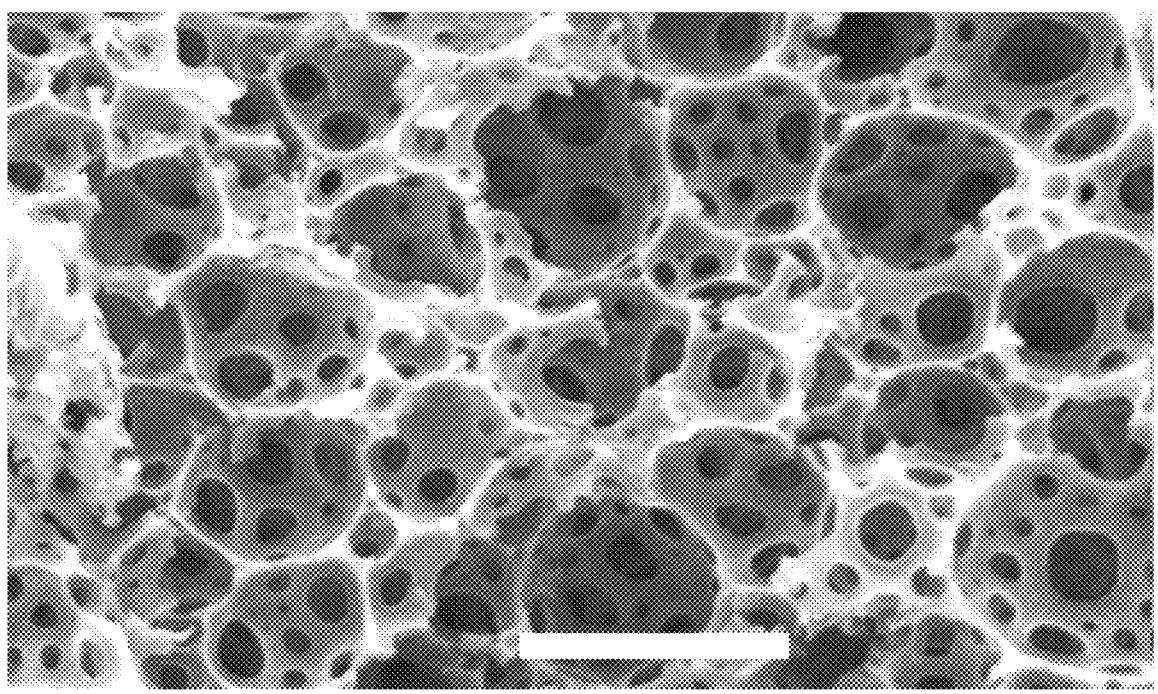
FIG. 9b shows SEM micrograph of natural collagen scaffold in accordance with the invention.

FIG. 9b shows SEM micrograph of natural collagen scaffold (N1, an embodiment of the present invention). Size of interconnecting pores were assessed using the added measurement bars, some of which are indicated by the fine lines in the micrograph. Scale bar represents 20 micron.

A SEM micrograph of a poly-HIPE structure is disclosed in Carnahan et al, Soft Matter 2006, 2, 608-616. The structure has generally spherical voids and circular pores. The voids and pores have a much smaller range of sizes and configurations than the liver tissue shown in FIG. 9a.

Figure 10:
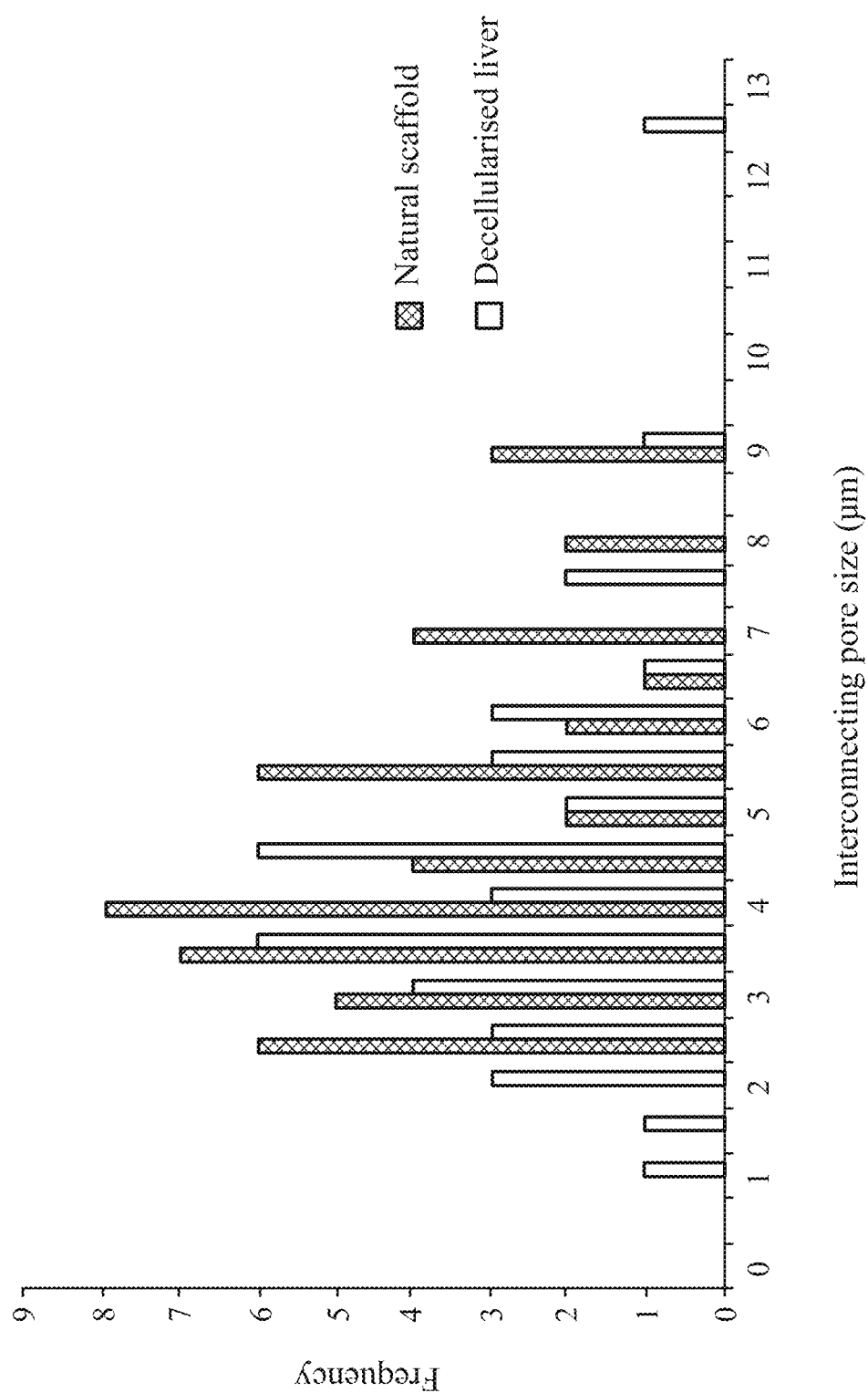
FIG. 10 is a bar chart showing interconnecting pore size distributions.

FIG. 10 is a bar chart showing interconnecting pore size distribution of decellularised liver tissue and natural collagen scaffold of the present invention. This Figure shows that the profile of the pore size distribution of the scaffold of the present closely reproduces that of liver tissue.

3.6 L929 Cell Viability

L929 cells cultured on the natural collagen scaffolds (N type) show good cell viability/growth over a culture period of 10 days. MTT absorbance values increase from 0.05 to 0.3 over the 10 day culture period. MTT viability assay was conducted. A blank scaffold (no cells) was run in parallel with each time point.

3.7 Culture of Primary Human Cells

Cultures were made of three primary human cell types (i.e. primary human hepatocytes (PHH), human liver cancer cell line HepG2 and primary human hepatic stellate cells) on the scaffolds of this invention. All cells cultured successfully. The natural collagen scaffolds of this invention is promoted improved phenotypes compared to synthetic scaffolds (S type). In particular, stellate cells cultured on the collagen scaffolds (N type) had reduced activation ("more in vivo like") compared to those cultured on traditional 2D hard plastic. The results clearly demonstrate that the natural collagen scaffolds (N type) which were manufactured by the method disclosed herein, were decidedly superior in maintaining desired gene expressions. The results are shown in Table 1.

TABLE 1

Gene expression changes in primary human hepatocytes cultured on 3D scaffolds.

| Scaffold type | Gene of interest | | | |
|---|---|---|---|---|
| | Albumin | HNF4a | CYP3A4 | NTCP |
| N1 | 17.82091 | 0.0273 | 0.078 | 0.013 |
| S1 | 38.34588 | 0.0086 | 0.008 | 0.000 |
| N4 | 9.059928 | 0.0113 | 0.107 | 0.017 |
| S4 | 260.2942 | 0.0095 | 0.046 | 0.002 |
| Thawed PHH | 274.6593 | 0.1763 | 1.417 | 0.504 |

Primary human hepatocytes were cultured for 7 days on 3D scaffolds (S1, S4, N1 and N4 [S=synthetic, N=natural]). Total RNA was extracted from all cells and analysed by QPCR for the expression of genes associated with hepatocyte function. Data shown are relative gene expression compared to GAPDH housekeeping gene and expressed as 2^-deltaCT. Maintaining expression of these genes (in comparison to thawed cells) is desired for optimal in vitro culture. Culture of cells on natural (N) scaffolds appeared to be preferential for maintaining hepatic gene expression, however expression was lower than in freshly thawed cells.

TABLE 2

Albumin gene expression in primary human hepatocytes and HepG2 cells cultured on natural 3D scaffolds.

| Scaffold type and cell type | Gene of interest Albumin |
|---|---|
| PHH-N1 | 17.82091 |
| PHH-N4 | 9.059928 |
| Thawed PHH | 274.6593 |
| HepG2-N1 | 29.64054647 |
| HepG2-N4 | 20.09131754 |

Primary human hepatocytes and HepG2 were cultured for 7 days on scaffolds of this invention (N1 and N4, N=natural). Total RNA was extracted from all cells and analysed by QPCR for the expression of albumin. Data shown are relative gene expression compared to GAPDH housekeeping gene and expressed as 2^-deltaCT. Maintaining expression of albumin expression (in comparison to thawed cells) is desired for optimal in vitro culture. Both cells types had comparable expression of albumin when cultured on the natural scaffolds, however this was still lower than expression in freshly thawed cells. The results are shown in Table 2.

TABLE 3

Gene expression changes in primary human hepatic stellate cells cultured on 3D scaffolds.

| | Gene of interest | | |
|---|---|---|---|
| Scaffold type | ACTA2 | COL1A1 | TGFβ |
| N1 | 0.165 | 0.165 | 0.092 |
| N4 | 0.450 | 0.566 | 0.117 |
| S1 | 2.054 | 40.45 | 0.837 |
| S4 | 1.894 | 41.01 | 0.815 |
| Pellet | 0.638 | 1.796 | 0.040 |
| 2D plastic | 0.417 | 3.637 | 0.061 |

Primary human hepatic stellate cells were cultured for 7 days either on standard plastic multi-well plates or on synthetic scaffolds of this invention (S1, S4, N1 and N4 [S=synthetic, N=natural]).

Total RNA was extracted from all cells and analysed by Taqman QPCR for the expression of genes associated with stellate cell activation. Data shown are relative gene expression compared to GAPDH housekeeping gene and expressed as 2^-deltaCT. Expression of these genes is maintained or promoted by culture on "hard" 2D plastic plates, but was reduced in samples cultured on natural (N) scaffolds. Cells cultured on synthetic (S) scaffolds had increased gene expression. Reduced expression of these genes is highly advantageous as it better represents in vivo conditions. The results are shown in Table 3.

The invention claimed is:
1. A method of forming a scaffold, comprising:
preparing a high internal phase emulsion (HIPE) comprising an aqueous solution of:

proteins selected from the group consisting of collagen and mixtures of collagen and chitosan; and,
a cross-linking agent;
wherein the preparing includes:
adding an immiscible organic solvent to the solution to form the HIPE as an oil-in-water emulsion;
reducing the temperature to solidify the HIPE;
removing water and organic solvent by vaporisation at a temperature above the melting point of the organic solvent to form a porous structure; and,
before or after the removing of the organic solvent, causing cross-linking of the protein with the cross-linking agent to form a crosslinked scaffold structure.

2. The method as claimed in claim 1, wherein the concentration of collagen in the aqueous solution is in the range of from about 2.5 wt % to about 20 wt %.

3. The method as claimed in claim 1, wherein the cross-linking reagent is selected from a group consisting of glutaraldehyde, genipin, carbodiimide, transglutaminase, chondroitin sulfate, dextran dialdehyde, bis(vinylsulfonyl) methane and hexamethylene di-isocyanate.

4. The method as claimed in claim 3, wherein the cross-linking agent is glutaraldehyde.

5. The method as claimed in claim 1, wherein the concentration of the cross-linking agent in the emulsion is in the range of from about 1 wt % to about 5 wt %.

6. The method as claimed in claim 1, wherein the immiscible organic solvent is selected from a group consisting of toluene and methylated tetrahydrofuran.

7. The method as claimed in claim 6, wherein the immiscible organic solvent is toluene.

8. The method as claimed in claim 1, wherein the adding is done at a temperature in the range of from about 30° C. to about 60° C.

* * * * *